(12) United States Patent
Zhang et al.

(10) Patent No.: US 12,376,803 B2
(45) Date of Patent: Aug. 5, 2025

(54) METHOD AND APPARATUS FOR HEART-LEVEL BLOOD PRESSURE ESTIMATION BASED ON ENSEMBLE LEARNING

(71) Applicant: Hong Kong Centre for Cerebro-Cardiovasculer Health Engineering Limited, Hong Kong (CN)

(72) Inventors: Yuanting Zhang, Hong Kong (CN); Nan Ji, Hong Kong (CN)

( * ) Notice: Subject to any disclaimer, the term of this patent is extended or adjusted under 35 U.S.C. 154(b) by 491 days.

(21) Appl. No.: 18/070,478

(22) Filed: Nov. 29, 2022

(65) Prior Publication Data
US 2024/0050043 A1    Feb. 15, 2024

(30) Foreign Application Priority Data

Aug. 10, 2022 (CN) .......................... 202210956086.X (51) Int. Cl.
*A61B 5/021* (2006.01)
*A61B 5/00* (2006.01)

(52) U.S. Cl.
CPC ............ *A61B 5/7278* (2013.01); *A61B 5/021* (2013.01); *A61B 5/7225* (2013.01); *A61B 5/7246* (2013.01); *A61B 5/7267* (2013.01)

(58) Field of Classification Search
CPC ..... A61B 5/021; A61B 5/7278; A61B 5/7225; A61B 5/7246; A61B 5/7267; A61B 5/6824

See application file for complete search history.

(56) References Cited

U.S. PATENT DOCUMENTS

| | | | |
|---|---|---|---|
| 2016/0302677 A1* | 10/2016 | He | A61B 5/0205 |
| 2019/0021611 A1* | 1/2019 | Kwon | A61B 5/02108 |
| 2019/0307339 A1* | 10/2019 | Aelen | A61B 5/7221 |
| 2020/0107763 A1* | 4/2020 | Antunes | A61B 5/0205 |
| 2021/0378529 A1* | 12/2021 | Colburn | A61B 5/7267 |

* cited by examiner

*Primary Examiner* — Eric F Winakur
(74) *Attorney, Agent, or Firm* — NCC-IP; Nevin Stuart Carmichael (57) ABSTRACT

The present invention relates to method and apparatus for heart-level blood pressure estimation based on ensemble learning. The invention relates to the technical field of biomedical technology. The method comprises: acquiring radial arterial blood pressure related information and a hydrostatic pressure of the radial artery of a subject; performing blood pressure conversion based on the radial arterial blood pressure related information and the hydrostatic pressure of the radial artery to obtain at least two brachial arterial blood pressure values; inputting the at least two brachial arterial blood pressure values into a trained correction model to obtain a target brachial arterial blood pressure value. The present invention realizes the conversion from a peripheral blood pressure, such as a radial arterial blood pressure measured by a wearable device, to a heart-level blood pressure, i.e. a brachial arterial blood pressure for clinical use, and performs feature fusion and a feature conversion on the feature information of each brachial arterial blood pressure value, so that the determined target brachial arterial blood pressure value becomes more accurate, and improves the accuracy and stability of the blood pressure estimation.

9 Claims, 7 Drawing Sheets

METHOD AND APPARATUS FOR HEART-LEVEL BLOOD PRESSURE ESTIMATION BASED ON ENSEMBLE LEARNING

FIELD OF THE INVENTION

The present invention relates to the field of biomedical technology, specifically, the present invention relates to a method and an apparatus for heart-level blood pressure estimation based on ensemble learning.

BACKGROUND OF THE INVENTION

Hypertension is a clinical syndrome characterized by increased blood pressure in the arteries of the body circulation, which may be accompanied by functional or organic damage to the heart, brain, kidneys and other organs. Hypertension is the most common chronic disease and the most important risk factor for cardiovascular disease. With the rapid increase in the number of patients, the diversity of causes and the expansion of the audience, the daily monitoring of human blood pressure is particularly important in the current trend of increasing attention to health care.

With the proliferation of patients, the diversity of causes and the expansion of the affected population, daily monitoring of blood pressure is particularly important with the current trend of increasing attention to health care.

Usually, brachial blood pressure is measured in the upper arm area, at the same height as the heart, but the measurement for the upper arm region is not convenient enough to achieve continuous daily monitoring. With the advancement of blood pressure monitoring technology, portable radial artery-based blood pressure measuring devices can meet the daily monitoring needs of users, but the measurements are easily affected by external factors such as arm posture when performing radial artery blood pressure measurement, resulting in unstable and low accuracy measurements.

OBJECTS OF THE INVENTION

An object of the present invention is to provide a method and an apparatus for heart-level blood pressure estimation based on ensemble learning.

The above object is met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

Embodiments of the present invention provide a method and an apparatus for heart-level blood pressure estimation based on ensemble learning that can solve the problem of blood pressure measurements in the prior art that are susceptible to the influence of human posture.

In a first main aspect, the present invention provides a method for heart-level blood pressure estimation based on ensemble learning, comprising:

acquiring radial arterial blood pressure related information and a hydrostatic pressure of the radial artery of a subject;

performing blood pressure conversion based on the radial arterial blood pressure related information and the hydrostatic pressure of the radial artery to obtain at least two brachial arterial blood pressure values;

inputting the at least two brachial arterial blood pressure values into a trained correction model, performing the following operations according to the correction model to obtain a target brachial arterial blood pressure value:

extracting feature information of each brachial arterial blood pressure value, and performing feature fusion on the feature information corresponding to the respective at least two brachial arterial blood pressure values to obtain fusion information;

performing feature transformation of the fusion information according to different levels of the correction model to obtain feature vectors of different dimensions;

determining a target feature vector according to the correlation among the feature vectors of difference dimensions;

determining the target brachial arterial blood pressure value corresponding to the target feature vector.

In a second main aspect, the present invention provides an apparatus for heart-level blood pressure estimation based on ensemble learning, comprising:

an acquiring module for acquiring radial arterial blood pressure related information and a hydrostatic pressure of the radial artery of a subject;

a conversion module for performing blood pressure conversion based on the radial arterial blood pressure related information and the hydrostatic pressure of the radial artery to obtain at least two brachial arterial blood pressure values;

a correction module for inputting the at least two brachial arterial blood pressure values into a trained correction model, performing the following operations according to the correction model to obtain a target brachial arterial blood pressure value:

extracting feature information of each brachial arterial blood pressure value, and performing feature fusion on the feature information corresponding to the respective at least two brachial arterial blood pressure values to obtain fusion information; performing feature transformation of the fusion information according to different levels of the correction model to obtain feature vectors of different dimensions; determining a target feature vector according to the correlation among the feature vectors of difference dimensions; determining the target brachial arterial blood pressure value corresponding to the target feature vector.

In a third main aspect, the present invention provides an electronic apparatus, comprising: a memory, a processor and a computer program stored in the memory, wherein the processor executes the computer program to implement the method steps in the first aspect of the embodiment of the present invention.

In a fourth main aspect, the present invention provides a computer readable storage medium in which a computer program is stored, wherein the computer program being executed by a processor to implement the method steps in the first aspect of the embodiment of the present invention.

The present invention performs blood pressure conversion based on the radial arterial blood pressure related information and the hydrostatic pressure of the radial artery to obtain at least two brachial arterial blood pressure values, then input the at least two brachial arterial blood pressure values into a trained correction model to obtain a target brachial arterial blood pressure value; the present invention realizes the conversion and correction of blood pressure measurement based on radial artery blood pressure related information and hydrostatic pressure of the radial artery by extracting feature information of each brachial arterial blood pressure value, and performing feature fusion on the feature information corresponding to the respective at least two brachial arterial blood pressure values to obtain fusion information; performing feature transformation of the fusion information according to different levels of the correction model to obtain feature vectors of different dimensions; determining a target feature vector according to the correlation among the feature vectors of difference dimensions; determining the target brachial arterial blood pressure value, i.e., the chest level blood pressure, corresponding to the target feature vector. The present invention can make the determined target brachial blood pressure value more accurate by performing feature fusion and feature transformation of the feature information of each brachial blood pressure value. Unlike the direct measurement of radial artery blood pressure values in prior art, which are susceptible to interference by external factors, the present invention realizes conversion of radial artery blood pressure measurement to brachial artery blood pressure values, improving the accuracy and stability of blood pressure estimation.

BRIEF DESCRIPTION OF THE DRAWINGS

The foregoing and further features of the present invention will be apparent from the following description of preferred embodiments which are provided by way of example only in connection with the accompanying figures, of which.

DESCRIPTION OF PREFERRED EMBODIMENTS

Embodiments of the present invention are described below referring to the drawings in the present invention. It should be understood that the embodiments described below in with referring to the drawings are exemplary descriptions for the purpose of explaining the technical solutions of the embodiments of the present invention and do not constitute a limitation of the technical solutions of the embodiments of the present invention.

It should be understood by those skilled in the art that, unless specifically stated, the singular forms "one", "a", "the" and "this" may also include the plural form. It should be further understood that the terms "includes" and "comprises" as used in embodiments of this invention mean that the corresponding features may be implemented as the features, information, data, steps, operations, components and/or assemblies presented, but do not exclude the implementation of other features, information, data, operations, components and/or assemblies that are supported in the art. It should be understood that when we refer to a component being "connected" or "coupled" to another component, the component may be directly connected or coupled to the other component, or it may refer to the component and the other component being connected through an intermediate component. In addition, the "connection" or "coupling" as used herein may include wireless connection or wireless coupling. The term "and/or" as used herein indicates at least one of the items defined by the term, for example, "A and/or B" may be implemented as "A" or as "B", or "A and B".

In order to make the purpose, technical solutions and advantages of the present invention clearer, the embodiments of present invention are described in further detail below referring to the drawings.

Ensemble learning is a class of machine learning frameworks that build and combine multiple learning algorithms to accomplish a learning task. The general structure is to generate a set of "individual learners" and then combine them with certain strategy. The combination strategies mainly include averaging, voting, and learning. The method for heart-level blood pressure estimation provided by the present invention is based on ensemble learning and can obtain accurate heart-level blood pressure measurement.

With recent advances in methods applied to blood pressure monitoring, the use of non-invasive wearable blood pressure monitors has become increasingly widespread. Traditional mercury sphygmomanometers and oscillometric sphygmomanometers are highly restrictive in terms of measurement status, requiring the subject to remain stationary, with the center of the cuff at the same height as the heart, without wearing thick clothing. In addition, mercury sphygmomanometers and oscillometric sphygmomanometers provide only a snapshot blood pressure value and are not suitable for continuous blood pressure monitoring.

It has been found that there are still many problems and challenges with non-invasive wearable blood pressure monitor: the emerging pulse wave transit time based cuffless blood pressure monitor, while providing beat-to-beat blood pressure measurements and being wearable and portable for daily use, also require the measuring position to be at the same height as the heart, limiting the use in other postures. Also, the accuracy of the measurements provided by the wearable blood pressure monitor needs to be improved.

The present invention provides a method, an apparatus, an electronic device, and a computer-readable storage medium for heart-level blood pressure estimation based on ensemble learning, and is intended to solve technical problems of the prior art as described above.

The technical solutions of the present invention and the technical effects resulting from the technical solutions of the present invention are described below through the description of several exemplary embodiments. It should be noted that the following embodiments can be cross-referenced, borrowed or combined with each other, and the descriptions of the same terms, similar features and similar implementation steps, etc. in different embodiments will not be repeated.

Figure 1:
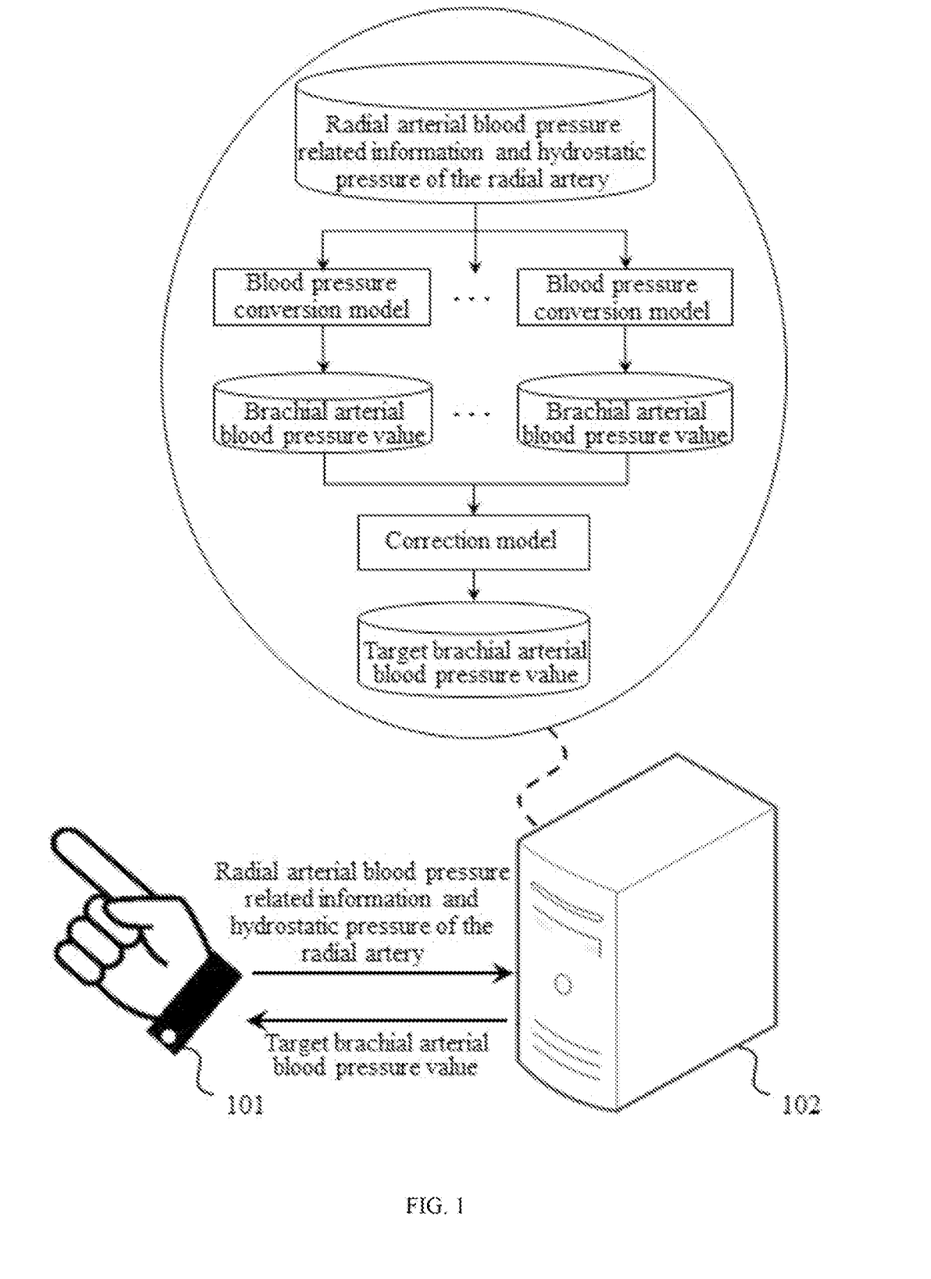
FIG. 1 shows a schematic diagram illustrating a method for heart-level blood pressure estimation based on ensemble learning provided by an embodiment of the present invention.

As shown in FIG. 1, the method for heart-level blood pressure estimation based on ensemble learning provided by the present invention can be applied in the scenario shown in FIG. 1. Specifically, the server 102 can obtain the radial artery blood pressure related information and the hydrostatic pressure of the radial artery of the subject from the client 101 (which runs in the wearable devices such as smart band), and through at least two blood pressure conversion models, perform blood pressure conversion based on the radial arterial blood pressure related information and the hydrostatic pressure of the radial artery to obtain at least two brachial arterial blood pressure values, then the above brachial artery blood pressure values are input to the trained correction model, and the correction model performs blood pressure correction based on each brachial artery blood pressure value to obtain a target brachial artery blood pressure value corresponding to the radial artery blood pressure related information, and then the server 102 returns the target brachial artery blood pressure value to the client 101 so that the client can obtain an accurate brachial artery blood pressure value.

In the scenario shown in FIG. 1, the method for heart-level blood pressure estimation based on ensemble learning can be performed in the server, and in other scenarios, it can also be performed in the terminal.

It is understood by those skilled in the art that the "terminal" used here can be a smart wearable device such as a cuff-type wearable device, or a watch, band, ring, etc.; the "server" can be a single server or a cluster of servers.

Figure 2:
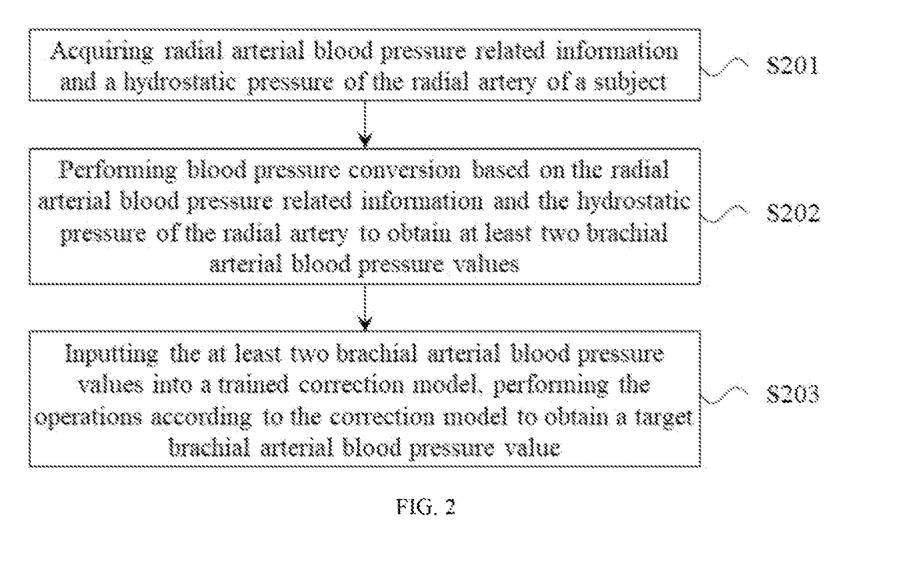
FIG. 2 shows a flowchart illustrating a method for heart-level blood pressure estimation based on ensemble learning provided by an embodiment of the present invention.

The present invention provides a method for heart-level blood pressure estimation based on ensemble learning, as shown in FIG. 2, which can be applied to a server or a terminal for blood pressure estimation, the method comprises: S201, acquiring radial arterial blood pressure related information and a hydrostatic pressure of the radial artery of a subject.

Specifically, the server or terminal for performing blood pressure estimation can obtain the hydrostatic pressure of the radial artery via a hydrostatic level sensor; the hydrostatic level sensor comprises at least one of an accelerometer and a gyroscope; the hydrostatic pressure is represented by a height and an angle of an arm of a target subject.

Meanwhile, the radial artery blood pressure related information is acquired by the peripheral artery blood pressure sensor, wherein the radial artery blood pressure related information includes at least one blood pressure signal value among the Korotkoff sound signal, the pressure signal, the photoplethysmogram signal, the electrocardiogram signal, the ultrasound signal, the bioelectromagnetic signal, and the bioimpedance signal.

S202, performing blood pressure conversion based on the radial arterial blood pressure related information and the hydrostatic pressure of the radial artery to obtain at least two brachial arterial blood pressure values.

Specifically, the server or terminal for performing the blood pressure estimation may input the radial artery blood pressure related information and the hydrostatic pressure of the radial artery into at least two blood pressure conversion models, process and convert the radial artery blood pressure related information and the hydrostatic pressure of the radial artery based on the blood pressure conversion models, and obtain one brachial artery blood pressure value corresponding to the output of each blood pressure conversion model. The processing steps of the blood pressure conversion models are described in detail below.

S203, inputting the at least two brachial arterial blood pressure values into a trained correction model, performing the following operations (1)-(3) according to the correction model to obtain a target brachial arterial blood pressure value; wherein, the correction model can be an artificial neural network-based model. A neural network is an operational model that consists of a large number of nodes (or neurons) interconnected with each other. Each node represents a specific output function, called the activation function. Each connection between two nodes represents a weighted value for the signal passing through that connection, called a weight, which represents the memory of an artificial neural network. The output of the network varies depending on the connection method, the weight value and the activation function. The network itself is usually an approximation of some algorithm or function of nature, or it may be an expression of a logical strategy. According to the topology of neural networks, they can be divided into feedforward and feedback networks.

Figure 3:
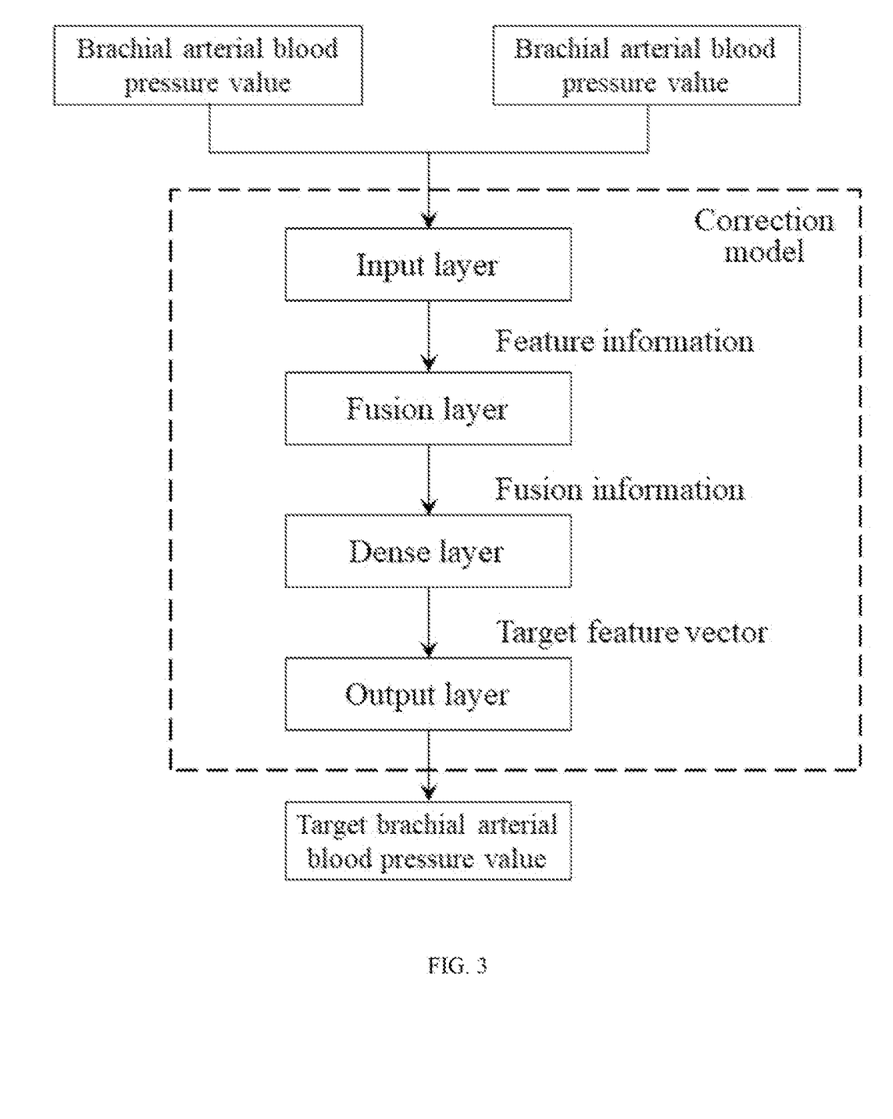
FIG. 3 shows a flowchart illustrating a data processing process of a correction model in a method for heart-level blood pressure estimation based on ensemble learning provided by an embodiment of the present invention.

Here the Multi-Layer Perception (MLP), a feedforward network, is used as an example for specific illustration of the correction model. As shown in FIG. 3, the correction model includes an input layer, a fusion layer, a dense layer and an output layer.

(1) Extracting feature information of each brachial arterial blood pressure value, and performing feature fusion on the feature information corresponding to the respective at least two brachial arterial blood pressure values to obtain fusion information.

Specifically, after acquiring at least two brachial artery blood pressure values, the input layer extracts the feature information of each brachial artery blood pressure value, and then performs feature fusion on each feature information based on the fusion layer to obtain the fusion information.

(2) Performing feature transformation of the fusion information according to different levels of the correction model to obtain feature vectors of different dimensions; determining a target feature vector according to the correlation among the feature vectors of difference dimensions.

Specifically, the dense layer is distributed with neurons of different levels, and the neurons of different levels are fully connected (i.e., any neuron of the upper level is connected to all neurons of the lower level), so the feature transformation of the fusion information can be performed based on the neurons of different levels, and the correlation among the feature vectors of difference dimensions can be determined based on the connection strength between neurons, i.e., the weight of each neuron, to obtain the output of the dense layer, i.e., the target feature vector.

(3) Determining the target brachial arterial blood pressure value corresponding to the target feature vector.

Specifically, the target feature vector can be classified based on the output layer to determine the target brachial artery blood pressure value.

The present invention performs blood pressure conversion based on the radial arterial blood pressure related information and the hydrostatic pressure of the radial artery to obtain at least two brachial arterial blood pressure values, then input the at least two brachial arterial blood pressure values into a trained correction model to obtain a target brachial arterial blood pressure value; the present invention realizes the conversion and correction of blood pressure measurement based on radial artery blood pressure related information and hydrostatic pressure of the radial artery by extracting feature information of each brachial arterial blood pressure value, and performing feature fusion on the feature information corresponding to the respective at least two brachial arterial blood pressure values to obtain fusion information; performing feature transformation of the fusion information according to different levels of the correction model to obtain feature vectors of different dimensions; determining a target feature vector according to the correlation among the feature vectors of difference dimensions; determining the target brachial arterial blood pressure value, i.e., the chest level blood pressure, corresponding to the target feature vector. The present invention can make the determined target brachial blood pressure value more accurate by performing feature fusion and feature transformation of the feature information of each brachial blood pressure value. Unlike the direct measurement of radial artery blood pressure values in prior art, which are susceptible to interference by external factors, the present invention realizes conversion of radial artery blood pressure measurement to brachial artery blood pressure values, improving the accuracy and stability of blood pressure estimation.

In an embodiment, performing blood pressure conversion based on the radial arterial blood pressure related information and the hydrostatic pressure of the radial artery to obtain at least two brachial arterial blood pressure values, comprises:
inputting the radial arterial blood pressure related information and the hydrostatic pressure of the radial artery into at least two blood pressure conversion models respectively to obtain a respective brachial arterial blood pressure value corresponding to each blood pressure conversion model; wherein, the blood pressure conversion models can be based on machine learning algorithms such as artificial neural networks, random forests, or Bayesian learning, which is not specifically limited in embodiments of the present invention.

In an embodiment, the radial arterial blood pressure related information comprises a radial arterial blood pressure related signal value; the at least two blood pressure conversion models comprise a physiological mathematical model and at least one machine learning model.

The physiological mathematical model determines the brachial artery blood pressure value based on the following method:
acquiring a relationship between the radial arterial blood pressure related signal value, the hydrostatic pressure and the brachial arterial blood pressure value indicated by the physiological mathematical model;
determining the brachial artery blood pressure value by calculation according to the relationship based on the radial arterial blood pressure related signal value and the hydrostatic pressure of the radial artery.

In the embodiment, the relationship between the radial artery blood pressure signal value, the hydrostatic pressure and the brachial artery blood pressure value can be characterized according to a predetermined function, and then the brachial artery blood pressure value is calculated by the predetermined function.

Figure 4:
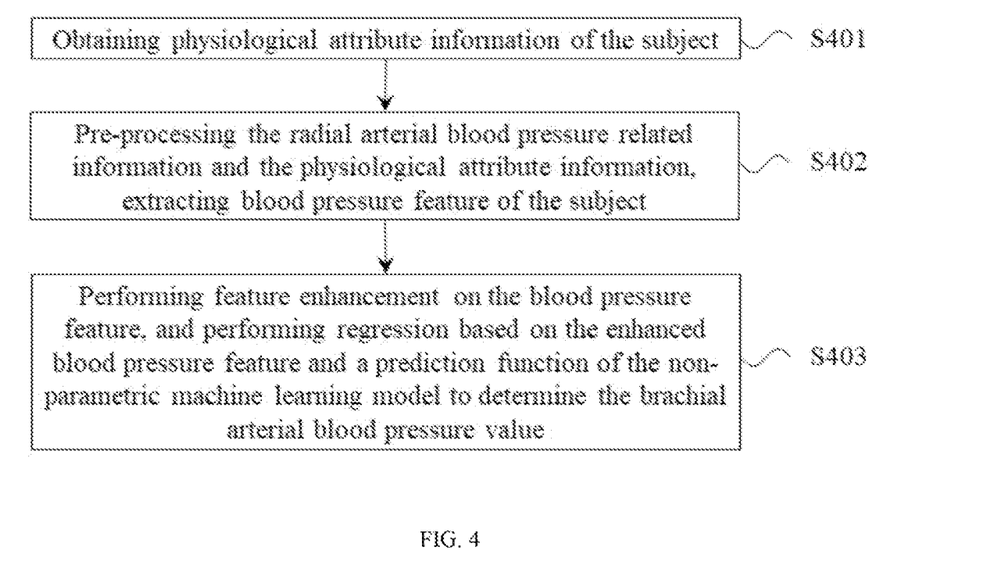
FIG. 4 shows a flowchart illustrating a data processing process of a second conversion model in a method for heart-level blood pressure estimation based on ensemble learning provided by an embodiment of the present invention.

In an embodiment, the at least one machine learning model comprises a non-parametric machine learning model, as shown in FIG. 4.

The non-parametric machine learning model comprises an input layer, a convolutional layer, a pooling layer and an output layer, the non-parametric machine learning model determines the brachial artery blood pressure value based on the following method:

S401, obtaining physiological attribute information of the subject; wherein, the physiological attribute information of the subject may include age, gender, smoking history, drinking habits, etc.

S402, pre-processing the radial arterial blood pressure related information and the physiological attribute information, extracting blood pressure feature of the subject.

Specifically, the radial artery blood pressure and physiological attribute information of the subject can be obtained by the input layer, and the information obtained can be pre-processed with data cleaning and feature transformation to obtain the blood pressure features of the subject.

S403, performing feature enhancement on the blood pressure feature, and performing regression based on the enhanced blood pressure feature and a prediction function of the non-parametric machine learning model to determine the brachial arterial blood pressure value; wherein, the prediction function is used to indicate a relationship between the enhanced blood pressure feature and the brachial arterial blood pressure value.

Specifically, the blood pressure features can be calculated based on the convolution layer to extract key features, and then feature selection and information filtering of the key features can be performed based on the pooling layer to obtain the enhanced feature information; followed by regression processing of the enhanced feature information based on the regression function in the output layer to obtain the brachial artery blood pressure value.

Figure 5:
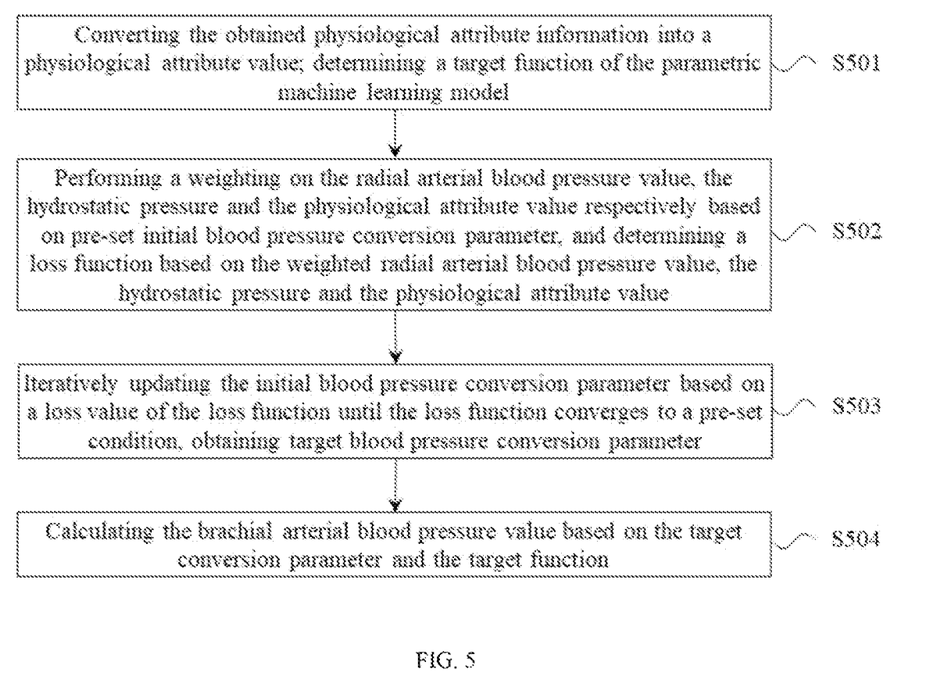
FIG. 5 shows a flowchart illustrating the determination of a second conversion model in a method for heart-level blood pressure estimation based on ensemble learning provided by an embodiment of the present invention.

In an embodiment, as shown in FIG. 5, the at least one machine learning model further comprises a parametric machine learning model.

The parametric machine learning model determines the brachial artery blood pressure value based on the following method:

S501, converting the obtained physiological attribute information into a physiological attribute value; and determining a target function of the parametric machine learning model; wherein the target function indicates the relationship between the radial arterial blood pressure related signal value, the hydrostatic pressure, the physiological attribute value and the brachial arterial blood pressure value;

S502, performing a weighting on the radial arterial blood pressure value, the hydrostatic pressure and the physiological attribute value respectively based on pre-set initial blood pressure conversion parameter, and determining a loss function based on the weighted radial arterial blood pressure value, the hydrostatic pressure and the physiological attribute value; wherein the loss function is used to indicate a difference between a calculated value and a true value of the brachial artery;

S503, iteratively updating the initial blood pressure conversion parameter based on a loss value of the loss function until the loss function converges to a pre-set condition, obtaining target blood pressure conversion parameter;

S504, calculating the brachial arterial blood pressure value based on the target conversion parameter and the target function.

In the embodiment, in order to improve the accuracy of blood pressure conversion, the radial artery blood pressure information and physiological attribute information are considered comprehensively to improve the reliability of the converted brachial artery blood pressure value from multiple dimensions.

In an embodiment, when both of the radial arterial blood pressure related signal value and the hydrostatic pressure of the radial artery are continuous time varying signals, the target brachial arterial blood pressure is a continuous time varying signal. Wherein the target brachial artery blood pressure value output by the correction model may be a tonoarteriogram (TAG) signal.

In the embodiment, when the radial artery blood pressure signal value and the hydrostatic pressure of the radial artery are discrete values, the target brachial artery blood pressure is also discrete values.

In an embodiment, the correction model is obtained by training based on the following method:
  determining sample brachial arterial blood pressure values and sample target values corresponding to the sample brachial arterial blood pressure values;
  inputting the sample brachial arterial blood pressure values into an initial correction model to obtain target blood pressure values outputted by the initial correction model; determining a target loss function based on the difference between the sample target value and the corresponding target blood pressure value;
  updating parameter of the initial correction model based on the difference until the target loss function converges to obtain the correction model.

The present invention performs blood pressure conversion based on the radial arterial blood pressure related information and the hydrostatic pressure of the radial artery to obtain at least two brachial arterial blood pressure values, then input the at least two brachial arterial blood pressure values into a trained correction model to obtain a target brachial arterial blood pressure value; the present invention realizes the conversion and correction of blood pressure measurement based on radial artery blood pressure related information and hydrostatic pressure of the radial artery by extracting feature information of each brachial arterial blood pressure value, and performing feature fusion on the feature information corresponding to the respective at least two brachial arterial blood pressure values to obtain fusion information; performing feature transformation of the fusion information according to different levels of the correction model to obtain feature vectors of different dimensions; determining a target feature vector according to the correlation among the feature vectors of difference dimensions; determining the target brachial arterial blood pressure value, i.e., the chest level blood pressure, corresponding to the target feature vector. The present invention can make the determined target brachial blood pressure value more accurate by performing feature fusion and feature transformation of the feature information of each brachial blood pressure value. Unlike the direct measurement of radial artery blood pressure values in prior art, which are susceptible to interference by external factors, the present invention realizes conversion of radial artery blood pressure measurement to brachial artery blood pressure values, improving the accuracy and stability of blood pressure estimation.

Figure 6:
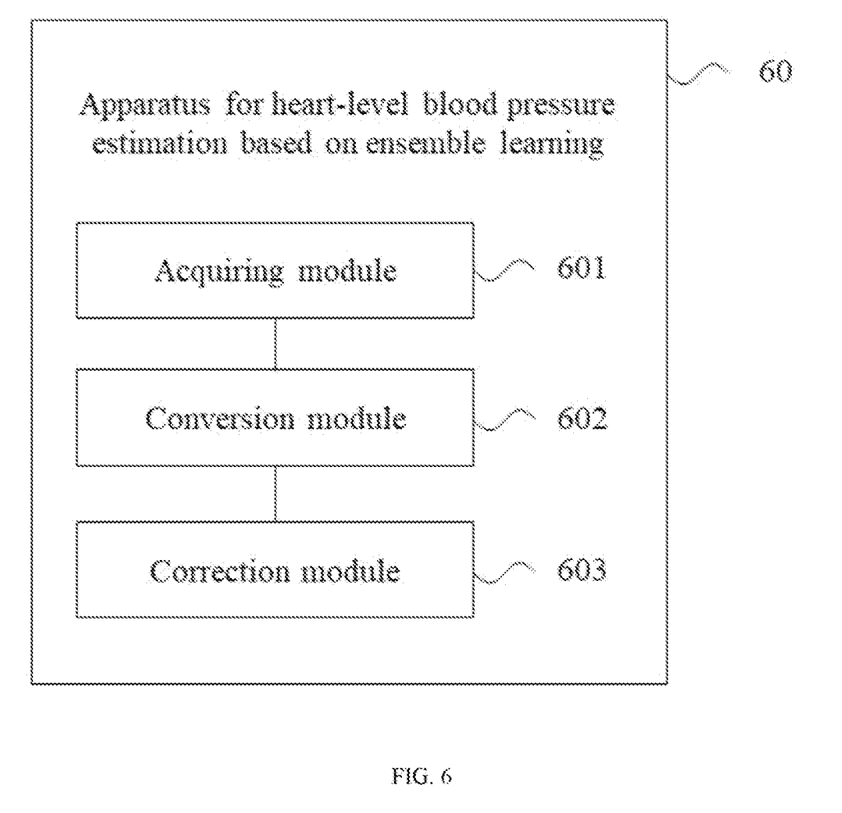
FIG. 6 shows a schematic diagram illustrating the structure of a device for heart-level blood pressure estimation based on ensemble learning provided by an embodiment of the present invention.

The present invention provides an apparatus for heart-level blood pressure estimation based on ensemble learning, as shown in FIG. 6, the apparatus for heart-level blood pressure estimation based on ensemble learning 60 may include:
  an acquisition module 601, a conversion module 602, and a correction module 603; wherein the acquiring module 601 for acquiring radial arterial blood pressure related information and a hydrostatic pressure of the radial artery of a subject;
  a conversion module 602 for performing blood pressure conversion based on the radial arterial blood pressure related information and the hydrostatic pressure of the radial artery to obtain at least two brachial arterial blood pressure values;
  a correction module 603 for inputting the at least two brachial arterial blood pressure values into a trained correction model, performing the following operations according to the correction model to obtain a target brachial arterial blood pressure value:
  extracting feature information of each brachial arterial blood pressure value, and performing feature fusion on the feature information corresponding to the respective at least two brachial arterial blood pressure values to obtain fusion information; performing feature transformation of the fusion information according to different levels of the correction model to obtain feature vectors of different dimensions; determining a target feature vector according to the correlation among the feature vectors of difference dimensions; determining the target brachial arterial blood pressure value corresponding to the target feature vector.

The device of the embodiments of the present invention can perform the method provided in the embodiments of the present invention with similar implementation principles, and the actions performed by the modules in the device of the embodiments of the present invention are corresponding to the steps in the method of the embodiments of the present invention, and the detailed functional descriptions of the modules of the device can be specifically referred to the descriptions in the corresponding methods shown in the previous section, which will not be repeated here.

The present invention performs blood pressure conversion based on the radial arterial blood pressure related information and the hydrostatic pressure of the radial artery to obtain at least two brachial arterial blood pressure values, then input the at least two brachial arterial blood pressure values into a trained correction model to obtain a target brachial arterial blood pressure value; the present invention realizes the conversion and correction of blood pressure measurement based on radial artery blood pressure related information and hydrostatic pressure of the radial artery by extracting feature information of each brachial arterial blood pressure value, and performing feature fusion on the feature information corresponding to the respective at least two brachial arterial blood pressure values to obtain fusion information; performing feature transformation of the fusion information according to different levels of the correction model to obtain feature vectors of different dimensions; determining a target feature vector according to the correlation among the feature vectors of difference dimensions; determining the target brachial arterial blood pressure value, i.e., the chest level blood pressure, corresponding to the target feature vector. The present invention can make the determined target brachial blood pressure value more accurate by performing feature fusion and feature transformation of the feature information of each brachial blood pressure value. Unlike the direct measurement of radial artery blood pressure values in prior art, which are susceptible to interference by external factors, the present invention realizes conversion of radial artery blood pressure measurement to brachial artery blood pressure values, improving the accuracy and stability of blood pressure estimation.

The present invention provides an electronic apparatus, comprising: a memory, a processor and a computer program stored in the memory, wherein the processor executes the computer program to implement the method steps of heart-level blood pressure estimation based on ensemble learning. Compared with the prior art for the brachial artery blood pressure measuring method, the present invention performs blood pressure conversion based on the radial arterial blood pressure related information and the hydrostatic pressure of the radial artery to obtain at least two brachial arterial blood pressure values, then input the at least two brachial arterial blood pressure values into a trained correction model to obtain a target brachial arterial blood pressure value; the present invention realizes the conversion and correction of blood pressure measurement based on radial artery blood pressure related information and hydrostatic pressure of the radial artery by extracting feature information of each brachial arterial blood pressure value, and performing feature fusion on the feature information corresponding to the respective at least two brachial arterial blood pressure values to obtain fusion information; performing feature transformation of the fusion information according to different levels of the correction model to obtain feature vectors of different dimensions; determining a target feature vector according to the correlation among the feature vectors of difference dimensions; determining the target brachial arterial blood pressure value, i.e., the chest level blood pressure, corresponding to the target feature vector. The present invention can make the determined target brachial blood pressure value more accurate by performing feature fusion and feature transformation of the feature information of each brachial blood pressure value. Unlike the direct measurement of radial artery blood pressure values in prior art, which are susceptible to interference by external factors, the present invention realizes conversion of radial artery blood pressure measurement to brachial artery blood pressure values, improving the accuracy and stability of blood pressure estimation.

Figure 7:
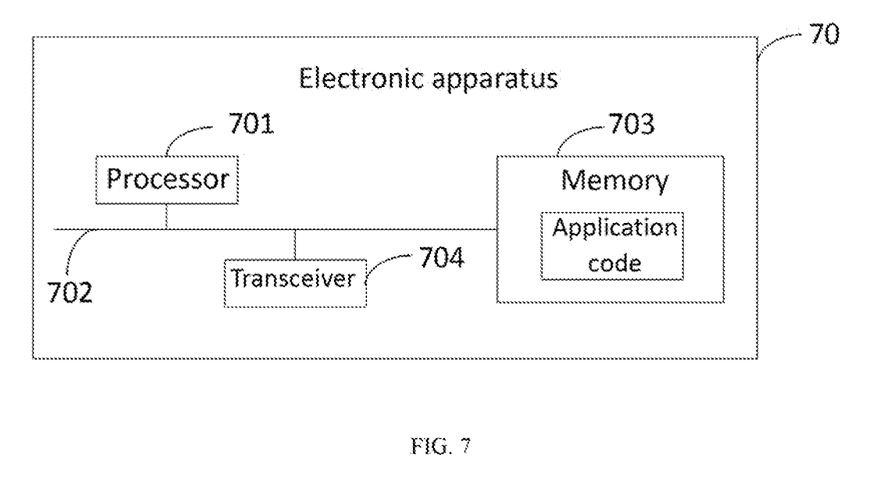
FIG. 7 shows a schematic diagram illustrating a structure of an apparatus for heart-level blood pressure estimation based on ensemble learning provided by an embodiment of the present invention.

In an optional embodiment, an electronic device is provided as shown in FIG. 7. The electronic device 700 comprises a processor 701 and a memory 703, wherein the processor 701 and the memory 703 are connected, e.g., via a bus 702. Optionally, the electronic device 700 may also include a transceiver 704. It is noted that the transceiver 704 is not limited to one in practical applications, and the structure of the electronic device 700 does not constitute a limitation of an embodiment of this invention.

The processor 701 may be a CPU (Central Processing Unit), a general-purpose processor, a DSP (Digital Signal Processor), an ASIC (Application Specific Integrated Circuit), an FPGA (FPGA), or a FPC (Fibre Optic Integrated Circuit). Integrated Circuit), FPGA (Field Programmable Gate Array) or other programmable logic device, transistorized logic device, hardware component, or any combination thereof. It may implement or execute various exemplary logic boxes, modules, and circuits described in conjunction with the disclosure of this invention. Processor 801 may also be a combination that implements computing function, such as a combination containing one or more microprocessors, a combination of a DSP and a microprocessor, etc.

The bus 702 may include a pathway to transfer information between above components. Bus 702 may be a PCI (Peripheral Component Interconnect) bus or an EISA (Extended Industry Standard Architecture) bus, for example. Bus 702 can be divided into address bus, data bus, control bus, etc. For the convenience of representation, only one thick line is used in FIG. 7, but it does not mean that there is only one bus or one type of bus.

Memory 703 can be ROM (Read Only Memory) or other types of static storage devices that can store static information and instructions, RAM (Random Access Memory) or other types of dynamic storage devices that can store information and instructions, or EEPROM (EEPROM (Electrically Erasable Programmable Read Only Memory), CD-ROM (Compact Disc Read Only Memory) or other optical disc storage, optical disc storage (including compressed disc, laser disc, optical disc, digital universal CD-ROM (Compact Disc Read Only Memory, read-only CD-ROM) or other optical disc storage, optical disc storage (including compact disc, laser disc, optical disk, digital universal disc, Blu-ray disc, etc.), disk storage media or other magnetic storage devices, or any other media capable of carrying or storing desired program code in the form of instructions or data structures and capable of being accessed by a computer, but not limited thereof.

Memory 703 is used to store the application program code for executing the present invention and is controlled for execution by processor 701. Processor 701 is used to execute the application program code stored in memory 703 to implement the method steps in the embodiment of the present invention.

The electronic apparatus includes, but is not limited to cuff-based wearable devices, and cuffless wearable devices such as watches, smart bands, rings, etc.

The present invention provides a computer readable storage medium in which a computer program is stored, wherein the computer program being executed by a processor to implement the method steps in the embodiment of the present invention.

The present invention provides a computer program product or computer program, the computer program product or computer program comprise computer instructions, which being stored in the computer readable storage medium. A processor of the computer device reads the computer instructions from the computer readable storage medium, and the processor executes the computer instructions such that the computer device, implement the following steps:

acquiring radial arterial blood pressure related information and a hydrostatic pressure of the radial artery of a subject;

performing blood pressure conversion based on the radial arterial blood pressure related information and the hydrostatic pressure of the radial artery to obtain at least two brachial arterial blood pressure values;

inputting the at least two brachial arterial blood pressure values into a trained correction model, performing the following operations according to the correction model to obtain a target brachial arterial blood pressure value;

extracting feature information of each brachial arterial blood pressure value, and performing feature fusion on the feature information corresponding to the respective at least two brachial arterial blood pressure values to obtain fusion information; performing feature transformation of the fusion information according to different levels of the correction model to obtain feature vectors of different dimensions; determining a target feature vector according to the correlation among the feature vectors of difference dimensions; determining the target brachial arterial blood pressure value corresponding to the target feature vector.

The terms "first" "second" "third" "fourth", "1", "2", etc. (if any) in the specification and claims of this invention and the accompanying drawings, are used to distinguish similar objects and not to describe a particular order or sequence. It should be understood that the number used is interchangeable where appropriate so that embodiments of the present invention can be implemented in an order other than that illustrated or described here.

It should be understood that although the individual steps in the flowchart of the accompanying drawings are shown sequentially as indicated by the arrows, the steps are not necessarily executed sequentially in the order indicated by the arrows. Unless being stated explicitly herein, in some embodiments of the present invention, the implementation steps in the respective flowcharts may be performed in other orders as needed. In addition, some or all of the steps in each flowchart may include multiple sub-steps or multiple phases based on actual application scenarios. Some or all of these sub-steps or phases may be executed at the same moment, and each of these sub-steps or phases may also be executed separately at different moments. In scenarios where the execution time is different, the order of execution of these sub-steps or phases can be flexibly configured as needed, and this embodiment is not limited in this regard.

The above description is only an optional implementation of part of the embodiments of the present invention. It should be noted that for a person with skill in the art, other similar means of implementation based on the technical principle of the present invention, and without deviating from the technical concept of the present invention, also fall within the scope of protection of the present invention.

We claim:

1. A method for heart-level blood pressure estimation based on ensemble learning, comprising:
   acquiring radial arterial blood pressure related information and a hydrostatic pressure of the radial artery of a subject;
   performing blood pressure conversion based on the radial arterial blood pressure related information and the hydrostatic pressure of the radial artery to obtain at least two brachial arterial blood pressure values;
   inputting the at least two brachial arterial blood pressure values into a trained correction model, performing the following operations according to the correction model to obtain a target brachial arterial blood pressure value;
   extracting feature information of each brachial arterial blood pressure value, and performing feature fusion on the feature information corresponding to the respective at least two brachial arterial blood pressure values to obtain fusion information;
   performing feature transformation of the fusion information according to different levels of the correction model to obtain feature vectors of different dimensions;
   determining a target feature vector according to the correlation among the feature vectors of difference dimensions;
   determining the target brachial arterial blood pressure value corresponding to the target feature vector.

2. The method according to claim 1, wherein the step of performing blood pressure conversion based on the radial arterial blood pressure related information and the hydrostatic pressure of the radial artery to obtain at least two brachial arterial blood pressure values comprises:
   inputting the radial arterial blood pressure related information and the hydrostatic pressure of the radial artery into at least two blood pressure conversion models respectively to obtain a respective brachial arterial blood pressure value corresponding to each blood pressure conversion model.

3. The method according to claim 2, wherein the radial arterial blood pressure related information comprises a radial arterial blood pressure related signal value; the at least two blood pressure conversion models comprise a physiological mathematical model and at least one machine learning model; the physiological mathematical model determines the brachial arterial blood pressure value based on the following method:
   acquiring a relationship between the radial arterial blood pressure related signal value, the hydrostatic pressure and the brachial arterial blood pressure value indicated by the physiological mathematical model;
   determining the brachial artery blood pressure value by calculation according to the relationship based on the radial arterial blood pressure related signal value and the hydrostatic pressure of the radial artery.

4. The method according to claim 3, wherein the at least one machine learning model comprises a non-parametric machine learning model; the non-parametric machine learning model determines the brachial arterial blood pressure value based on the following method:
   obtaining physiological attribute information of the subject;
   pre-processing the radial arterial blood pressure related information and the physiological attribute information, extracting blood pressure feature of the subject;
   performing feature enhancement on the blood pressure feature, and performing regression based on the enhanced blood pressure feature and a prediction function of the non-parametric machine learning model to determine the brachial arterial blood pressure value;
   wherein the prediction function is used to indicate a relationship between the enhanced blood pressure feature and the brachial arterial blood pressure value.

5. The method according to claim 3, wherein the at least one machine learning model further comprises a parametric machine learning model; the parametric machine learning model determines the brachial arterial blood pressure value based on the following method:
   converting the obtained physiological attribute information into a physiological attribute value;
   determining a target function of the parametric machine learning model; wherein the target function indicates the relationship between the radial arterial blood pressure related signal value, the hydrostatic pressure, the physiological attribute value and the brachial arterial blood pressure value;
   performing a weighting on the radial arterial blood pressure value, the hydrostatic pressure and the physiological attribute value respectively based on pre-set initial blood pressure conversion parameter, and determining a loss function based on the weighted radial arterial blood pressure value, the hydrostatic pressure and the physiological attribute value;
   the loss function is used to indicate a difference between a calculated value and a true value of the brachial artery;
   iteratively updating the initial blood pressure conversion parameter based on a loss value of the loss function until the loss function converges to a pre-set condition, obtaining target blood pressure conversion parameter;
   calculating the brachial arterial blood pressure value based on the target conversion parameter and the target function.

6. The method according to claim 3, wherein when both of the radial arterial blood pressure related signal value and the hydrostatic pressure of the radial artery are continuous time varying signals, the target brachial arterial blood pressure is a continuous time varying signal.

7. The method according to claim 1, wherein the correction model is obtained by training based on the following method:
   determining sample brachial arterial blood pressure values and sample target values corresponding to the sample brachial arterial blood pressure values;

inputting the sample brachial arterial blood pressure values into an initial correction model to obtain target blood pressure values outputted by the initial correction model;

determining a target loss function based on the difference between the sample target value and the corresponding target blood pressure value;

updating parameter of the initial correction model based on the difference until the target loss function converges to obtain the correction model.

8. An electronic apparatus, comprising: a memory, a processor and a computer program stored in the memory, wherein the processor executes the computer program to implement the method steps of claim 1.

9. An apparatus for heart-level blood pressure estimation based on ensemble learning, comprising:

an acquiring module for acquiring radial arterial blood pressure related information and a hydrostatic pressure of the radial artery of a subject;

a conversion module for performing blood pressure conversion based on the radial arterial blood pressure related information and the hydrostatic pressure of the radial artery to obtain at least two brachial arterial blood pressure values;

a correction module for inputting the at least two brachial arterial blood pressure values into a trained correction model, performing the following operations according to the correction model to obtain a target brachial arterial blood pressure value:

extracting feature information of each brachial arterial blood pressure value, and performing feature fusion on the feature information corresponding to the respective at least two brachial arterial blood pressure values to obtain fusion information; performing feature transformation of the fusion information according to different levels of the correction model to obtain feature vectors of different dimensions; determining a target feature vector according to the correlation among the feature vectors of difference dimensions; determining the target brachial arterial blood pressure value corresponding to the target feature vector.

* * * * *